US011485806B2

(12) United States Patent
Sripothongnak et al.

(10) Patent No.: US 11,485,806 B2
(45) Date of Patent: Nov. 1, 2022

(54) PROCESS FOR THE PREPARATION OF POLYMERIZED POLYETHYLENE WAX

(71) Applicant: SCG Chemicals Co., Ltd., Bangkok (TH)

(72) Inventors: Saovalak Sripothongnak, Bangkok (TH); Thawesak Parawan, Bangkok (TH); Nittiphat Nealmongkolrattana, Bangkok (TH); Tossapol Khamnaen, Bangkok (TH); Sumate Charoenchaidet, Bangkok (TH)

(73) Assignee: SCG Chemicals Co., Ltd., Bangkok (TH)

( * ) Notice: Subject to any disclaimer, the term of this patent is extended or adjusted under 35 U.S.C. 154(b) by 0 days.

(21) Appl. No.: 16/347,690

(22) PCT Filed: Nov. 6, 2017

(86) PCT No.: PCT/EP2017/078290
§ 371 (c)(1),
(2) Date: May 6, 2019

(87) PCT Pub. No.: WO2018/083290
PCT Pub. Date: May 11, 2018

(65) Prior Publication Data
US 2019/0263947 A1    Aug. 29, 2019

(30) Foreign Application Priority Data

Nov. 7, 2016 (EP) .................................... 16197563

(51) Int. Cl.
*C08F 110/02* (2006.01)
*C07C 2/34* (2006.01)
(Continued)

(52) U.S. Cl.
CPC .............. *C08F 110/02* (2013.01); *C07C 2/34* (2013.01); *C07F 5/068* (2013.01); *C08F 10/00* (2013.01);
(Continued)

(58) Field of Classification Search
CPC ........ C08F 110/02; C08F 10/00; C08F 10/02; C08F 210/18; C08F 210/02; C08F 210/16;
(Continued)

(56) References Cited

U.S. PATENT DOCUMENTS 5,665,818 A *  9/1997  Tilston .................. C08F 210/16
                                                        525/247
6,100,213 A    8/2000  Kumamoto et al.
(Continued)

FOREIGN PATENT DOCUMENTS

EP       0890583 A1   1/1999
EP       0985673 A2   3/2000
(Continued)

OTHER PUBLICATIONS

Feb. 8, 2018—ISR & WO PCT/EP2017/078290.
(Continued)

*Primary Examiner* — Ali Z Fadhel
(74) *Attorney, Agent, or Firm* — Banner & Witcoff, Ltd.

(57) ABSTRACT

The present invention relates to a process for the preparation of a polyethylene wax, the process comprising the steps of providing a catalyst solution, wherein the catalyst solution comprises at least one activating compound, an alkylaluminoxane and a me-tallocene complex, wherein the molar ratio of the activating compound to aluminum comprised in the alkylaluminoxane is from 0.0005 to 0.20; and polymerizing ethylene, by contacting the ethylene and the catalyst solution.

20 Claims, 1 Drawing Sheet

Figure 1:
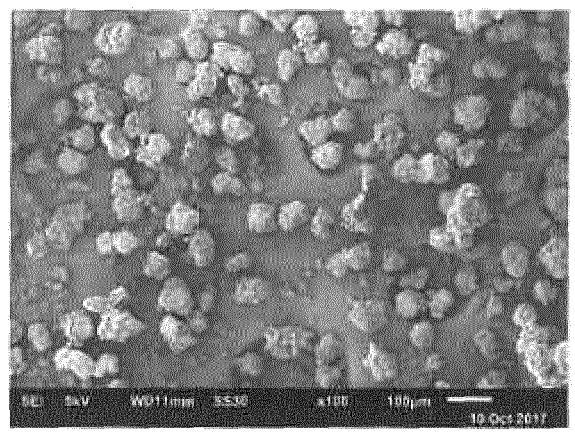

(51) Int. Cl.
| | |
|---|---|
| *C07F 5/06* | (2006.01) |
| *C08F 210/18* | (2006.01) |
| *C08F 210/02* | (2006.01) |
| *C08F 210/16* | (2006.01) |
| *C08F 210/00* | (2006.01) |
| *C08F 10/00* | (2006.01) |
| *C08F 10/02* | (2006.01) |
| *C08F 293/00* | (2006.01) |
| *C08F 4/00* | (2006.01) |
| *C08F 2/04* | (2006.01) |

(52) U.S. Cl.
CPC ............ *C08F 10/02* (2013.01); *C08F 210/00* (2013.01); *C08F 210/02* (2013.01); *C08F 210/16* (2013.01); *C08F 210/18* (2013.01); *C07C 2531/14* (2013.01); *C07C 2531/22* (2013.01); *C08F 2/04* (2013.01); *C08F 4/00* (2013.01); *C08F 293/00* (2013.01); *C08F 2410/00* (2013.01); *C08F 2410/01* (2013.01); *C08F 2420/00* (2013.01)

(58) Field of Classification Search
CPC .. C08F 210/00; C08F 4/00; C08F 2/04; C08F 2410/00; C08F 2420/00; C08F 293/00; C08F 2410/01; C07F 5/068; C07C 2/34; C07C 2531/14; C07C 2531/22
See application file for complete search history.

(56) References Cited

U.S. PATENT DOCUMENTS

| | | | | |
|---|---|---|---|---|
| 6,281,320 | B1* | 8/2001 | Kao | ............... C08F 10/00 526/348 |
| 8,895,465 | B2 | 11/2014 | Luo | |
| 2006/0223960 | A1* | 10/2006 | Jaber | ............... C08F 10/00 526/153 |
| 2008/0287617 | A1* | 11/2008 | Holtcamp | ............... C08F 10/00 526/116 |
| 2017/0291973 | A1* | 10/2017 | Munro | ............... C07F 5/068 |

FOREIGN PATENT DOCUMENTS

| | | |
|---|---|---|
| EP | 2933277 A1 | 10/2015 |
| WO | 99/30819 A1 | 6/1999 |

OTHER PUBLICATIONS

Jul. 1, 2015—Manteghi, Amin et al., "Synthesis, characterization, rheological and thermal behavior of metallocene ethylene-norbornene copolymers with low norbornene content using pentafluorophenol modified methylaluminoxane" Polymen International, vol. 64, No. 7.

Nov. 14, 2005—Masayuki Fujita et al., "Propylene Polymerization Using ansa-Zirconocenes with Water-Pentafluorophenol-Modified Methylaluminoxane" macromolecular Chemistry and Physics, vol. 206, No. 22, p. 2278-2283.

\* cited by examiner

PROCESS FOR THE PREPARATION OF POLYMERIZED POLYETHYLENE WAX

CROSS-REFERENCE TO RELATED APPLICATIONS

This application is a U.S. National Stage application under 35 U.S.C. § 371 of International Application PCT/EP2017/078290 (published as WO 2018/083290 A1), filed Nov. 6, 2017, which claims the benefit of priority to Application EP 16197563.6, filed Nov. 7, 2016. Benefit of the filing date of each of these prior applications is hereby claimed. Each of these prior applications is hereby incorporated by reference in its entirety.

The present invention relates to a process for the preparation of a polyethylene wax, the said process for producing a polymerized polyethylene wax using a novel catalyst solution in a polymerization step, the novel catalyst solution prepared under suitable process conditions and the polymerized polyethylene wax obtainable this way.

A variety of processes for preparing polymerized polyethylene waxes are provided in the prior art. Respective conventional polymerization processes are, for example, gas phase, slurry, solution or high pressure polymerization processes. It is known that a homogeneous polymerization process for producing polyethylene wax is conducted by a solution polymerization. In contrast to that, gas phase and slurry polymerization processes are heterogeneous polymerization processes of phase mixtures, wherein the slurry polymerization process is extensively practiced in an industrial scale to prevent the fouling effects in polymerization reactors.

A catalyst solution containing a metallocene complex is used in a large scale for producing olefin polymers such as polyethylene, polypropylene and other relevant polymers by the said conventional polymerization processes. For example, US 2006/0223960 A1 describes a cocatalyst system based on a halogenated phenol and an organometallic catalyst containing at least one π-ligand known as metallocene catalyst which is activated by using a modified methylahlumninoxane (MAO) and an additional aluminum alkyl. The cocatalyst system is an attractive lower-cost activator organoboron activators, by having the ability to improve the activity and stability under in comparison with the slurry or gas phase polymerization conditions.

U.S. Pat. No. 6,100,213 A describes a solid catalyst component containing an aluminum compound obtained by contacting a carrier with an organoaluminoxy compound followed by contacting with a compound having an electron attractive group. Said solid catalyst component containing an aluminum compound is used for contacting with a transition metal compound to obtain a catalyst for olefin polymerization. The catalyst has a high polymerization activity in the process of slurry or gas phase polymerization and provides an olefin polymer with excellent particle properties.

U.S. Pat. No. 8,895,465 B2 describes the preparation of an activator precursor compositions and respective activator compositions as well as their use as catalysts. The activator precursor compositions comprise a support material contacted with an organoaluminum compound and polyfunctional compounds having at least two aromatic groups and containing at least one polar monoprotic group on each said aromatic group. The activator compositions are prepared from a support material, an organoaluminum compound, an aluminoxane and a polyfunctional compound having at least two aromatic groups containing at least one polar monoprotic group on each said aromatic group. The activator precursor compositions and activator compositions result in catalyst systems having high efficiency. The compositions are stable under inert and anhydrous conditions. The compositions are normally in solid form and also perform significantly better than typical supported aluminoxanes when being used as cocatalysts in a slurry or gas phase polymerization process. The activator precursor compositions is contacted with metallocenes to yield in highly active catalyst systems. Said catalyst systems give the controllable content of aluminum loadings in a range comparable to or near 60% more than a typical system activated with a commercially available supported methylaluminoxane and increase activity more than 200-400% compared with the typical systems.

In light of the prior art, it is, therefore, the object of the present invention to provide a process for the preparation of a polyethylene wax and a novel catalyst solution overcoming drawbacks of the prior art. In particular, catalyst systems and processes for the preparation of polyethylene wax shall be provided resulting in high polymerization activity, providing the possibility to control size and morphology of the olefin wax, in particular of solid olefin wax.

The object is first of all achieved by a process for the preparation of a polyethylene wax, the process comprising the steps:
i) providing a catalyst solution,
wherein the catalyst solution comprises at least one activating compound, an alkyl-aluminoxane and a metallocene complex, wherein the molar ratio of the activating compound to aluminum comprised in the alkylaluminoxane is from 0.0005 to 0.20; and
ii) polymerizing ethylene, by contacting the ethylene and the catalyst solution.

Preferably, the activating compound is selected from the group consisting of phenols, alcohols, sulfonic acids, sulfonates, boronic acids, boronates, heterocycles, amines, amides and nitriles.

Preferably, the activating compound is selected from the group consisting of phenol, 2,6-bis (tert-butyl)-4-methylphenol, 2,3,4,5,6-pentafluorophenol, 2,3,5,6-tetrafluorophenol, 2,4,6-trifluorophenol, 2,5-difluorophenol, 3,5-difluorophenol, 4-fluorophenol, 3,5-bis(trifluoromethyl)phenol, trifluoromethanol, 1,1,2,2,2-pentafluoroethanol, 2,2,2-trifluoroethanol, 1,1,1,3,3,3-hexafluoro-2-(trifluoromethyl)propan-2-ol, 1,1,1,3,3,3-hexafluoropropan-2-ol, 1,1,1-trifluoropropan-2-ol, 2,2,3,3-tetrafluoropropan-1-ol, 2,2,3,3,3-pentafluoropropan-1-ol, 1,3-difluoropropan-2-ol, methanesulfonic acid, 4-methylbenzenesulfonamide, 4-methylbenzenesulfonic acid, trifluoromethanesulfonic acid, 4-fluorophenylboronic acid, phenylboronic acid, pyridine, 1H-indole and mixtures thereof.

Furthermore, it is preferred, that the alkylaluminoxane is selected from methylaluminoxane, i-butyl methylaluminoxane, n-butyl methylaluminoxane and n-hexyl methylaluminoxane.

Preferably, the metallocene complex contains at least one cyclopentadienyl ligand bonded to a transition metal selected from zirconium, titanium and hafnium.

Preferably, the metallocene complex is selected from Bis(n-butylcyclopentadienyl)zirconium (IV)dichloride and (dimethylsilylene)bis(2-methyl-4,5-benzoindenyl)zirconium(IV)dichloride.

Preferably, the catalyst solution further comprises an aliphatic hydrocarbon solvent or an aromatic hydrocarbon solvent or mixture thereof.

Preferably, the molar ratio of the activating compound to the aluminium comprised in the alkylaluminoxane is from 0.002 to 0.15 and more preferably from 0.09 to 0.12.

Preferably, a molar ratio of the aluminum comprised in the alkylaluminoxane to a metal comprised in the metallocene complex is from 25 to 200, preferably from 50 to 200 and more preferably from 50 to 100.

In preferred embodiments the polymerizing is slurry polymerization.

Furthermore, it is preferred that the polymerizing comprises contacting the catalyst solution contacting with ethylene, hydrogen and at least one comonomer having 3 to 10 carbon atoms at a temperature from 40 to 90° C. and a pressure from 1 to 12 bar in a hydrocarbon solvent.

Preferably, a molar ratio of hydrogen to ethylene is from 0.005 to 0.05.

Finally, the polyethylene wax has a molecular weight from 500 to 20,000 g/mol, a molecular weight distribution from 2 to 4, a density from 0.91 to 0.98 g/mL and a viscosity from 10 to 25,000 cP.

The process of the present invention comprises the steps of providing a catalyst solution and polymerizing ethylene. The provided catalyst solution comprises at least one activating compound, an alkylaluminoxane and a metallocene complex. The resultant mixture has to be soluble in an aliphatic hydrocarbon solvent or an aromatic hydrocarbon solvent or a mixture thereof. The molar ratio of the activating compound to aluminum comprised in the alkylaluminoxane is from 0.0005 to 0.20, preferably from 0.002 to 0.15 and more preferably from 0.09 to 0.12. The optimum molar ratio of the activating compound to the aluminum comprised in the alkylaluminoxane of the said catalyst solution has a significant influence on the catalytic activity. In comparison with a catalyst solutions without the activating compound the inventive catalyst solution shows much higher activity.

The molar ratio of the aluminum comprised in the alkylaluminoxane to a metal comprised in the metallocene complex is from 25 to 200, preferably from 50 to 200 and more preferably from 50 to 100. These preferred ratios are also suitable to increase the activity of the catalyst solution.

Furthermore, the addition of triisobutylaluminum to the catalyst solution leads to enhanced activity. The compositions are prepared to produce a homogeneous catalyst solution before conducting a slurry polymerization process under suitable process conditions in a hydrocarbon solvent to produce the polyethylene wax.

The present invention concerns the preparation process for a polymerized polyethylene wax by using a homogeneous catalyst solution in a slurry polymerization process. In order for increasing the activity of the polymerized polyethylene wax, the composition development of the homogeneous catalyst solution has been investigated.

Suitable process conditions of the slurry polymerization process are employed to produce the polyethylene wax. These conditions comprise contacting the homogeneous catalyst solution with ethylene, hydrogen and at least one comonomer having 3 to 10 carbon atoms at a temperature from 40 to 90° C. and a pressure from 1 to 12 bar in a hydrocarbon solvent. The slurry polymerization process is conducted in at least one polymerization reactor.

The detailed embodiments and features of this present invention will be further described in the detailed description of the invention and the appended claims.

DETAILED DESCRIPTION OF THE INVENTION

The catalyst solution of the present invention comprises three significant constituents which are described in detail below.

1. Activating Compound

The term "activating compound" as used herein refers to the compounds preferably selected from phenols, alcohols, sulfonic acids, sulfonates, boronic acids, boronates, heterocycles, amines, amides and nitriles.

In an embodiment, the phenols are alkylphenols and halogenated phenols.

The term "alkyl" as used herein includes a straight or branched chain alkyl moieties, typically having 1, 2, 3, 4, 5 or 6 carbon atoms and also refers to groups such as methyl, ethyl, propyl (n-propyl or isopropyl), butyl (n-butyl, sec-butyl or tert-butyl), pentyl (including neopentyl), hexyl and the like. Additionally, the term "halogenated" or "halogen" or "halo" refers to F, Cl, Br or I. Preferably, "halogenated" is F or Cl, wherein F is more preferably.

In another embodiment, the alcohols are halogenated alcohols.

In another embodiment, the sulfonic acids are aliphatic sulfonic acids are aromatic sulfonic acids, preferably methane sulfonic acid, trifluoromethanesulfonic acid, p-toluene sulfonic acid.

In another embodiment, the sulfonates are aliphatic sulfonates or aromatic sulfonates, preferably aliphatic methanesulfonates, p-toluene sulfonates and trifluoromethanesulfonates.

In another embodiment, the boronic acids are aliphatic boronic acids or aromatic boronic acids.

In another embodiment, the boronates are aliphatic boronates or aromatic boronates.

In another embodiment, the heterocycles are azirinyls, oxiranyls, 1,2-oxathiolanyl, imidazolyls, thienyls, furyls, tetrahydrofuryls, pyranyls, thiopyranyls, thianthrenyls, isobenzofuranyls, benzofuranyls, chromenyls, pyrrolyls, pyrrolinyls, pyrrolidinyls, imidazolyls, imidazolidinyls, benzimidazolyls, pyrazolyls, pyrazinyls, pyrazolidinyls, thiazolyls, isothiazolyls, dithiazolyls, oxazolyls, isoxazolyls, pyridyls, pyrazinyls, pyrimidinyls, piperidyls, piperazinyls, pyridazinyls, morpholinyls, thiomorpholinyls, thiomorpholinos, indolizinyls, isoindolyls, indolyls, benzimidazolyls, cumaryls, indazolyls, triazolyls, tetrazolyls, purinyls, 4H-quinolizinyl, isoquinolyls, quinolyls, tetrahydroquinolyls, tetrahydroisoquinolyls, decahydroquinolyls, octahydroisoquinolyls, benzofuranyls, dibenzofuranyl, benzothiophenyls, dibenzothiophenyls, phthalazinyls, naphthyridinyls, quinoxalyls, quinazolinyls, quinazolinyls, cinnolinyls, pteridinyls, carbazolyls, β-carbolinyls, phenanthridinyls, acridinyls, perimidinyls, phenanthrolinyls, furazanyls, phenazinyls, phenothiazinyls, phenoxazinyls, chromenyls, isochromanyls, chromanyls and the like.

In a particularly preferred embodiment, the activating compound is selected from of phenol, 2,6-bis(1,1-dimethylethyl)-4-methylphenol, 2,3,4,5,6-pentafluorophenol, 2,3,5,6-tetrafluorophenol, 2,4,6-trifluorophenol, 2,5-difluorophenol, 3,5-difluorophenol, 4-fluorophenol, 3,5-bis(trifluoromethyl)phenol, trifluoromethanol, 1,1,2,2,2-pentafluoroethanol, 2,2,2-trifluoroethanol, 1,1,1,3,3,3-hexafluoro-2-(trifluoromethyl)propan-2-ol, 1,1,3,3,3-hexafluoropropan-2-ol, 1,1,1-trifluoropropan-2-ol, 2,2,3,3-tetrafluoropropan-1-ol, 2,2,3,3,3-pentafluoropropan-1-ol, 1,3-difluoropropan-2-ol, methanesulfonic acid, 4-methylbenzenesulfonamide, 4-methylbenzenesulfonic acid, trifluoromethanesulfonic acid, 4-fluorophenylboronic acid, phenylboronic acid, pyridine, 1H-indole and mixtures thereof.

The selection of the molar amount of the activating compound has a significant influence on the activity of the polymerized polyethylene wax. Typically, it is selected in a range of the molar ratio of at least one activating compound to aluminum comprised in the alkylaluminoxane.

Normally and preferably, the use of an excessive molar amount of activating compound should be avoided due to the deterioration of polymerization activity.

2. Alkylaluminoxane

The term "alkyl" as used herein includes straight or branched chain alkyl moieties, typically having 1 to 10 carbon atoms and also refers to groups such as methyl, ethyl, propyl (n-propyl or i-propyl), butyl (n-butyl, sec-butyl or tert-butyl), pentyl (including neopentyl), hexyl, octyl and the like. Preferably, an alkyl may have 1, 2, 3, 4, 5 or 6 carbon atoms. More preferably, the alkyl contains one carbon atom, i.e. methyl groups.

The term "aluminoxane" as used herein refers to an activator for an olefin polymerization process prepared by partial hydrolysis of aluminum compounds such as alkyl aluminum compounds with a water-containing source, in which the aluminoxane contains a unit denoted by the formula below (I):

$$\mathrm{-[(R)AlO]}_n\mathrm{-} \qquad (I)$$

wherein R is an alkyl group and n is an integer of from 5 to 200.

The alkylaluminoxane used in the present invention is preferably selected from "methylaluminoxane (MAO)" and "modified methylaluminoxane (MMAO)".

In an embodiment, the alkylaluminoxane is MAO, i.e. the R group of the above formula is methyl MAO is prepared by partial hydrolysis of trimethyl aluminum together with a water-containing source which is provided as the hydrolyzing agent in the synthetic procedure.

In another embodiment, the alkylaluminoxane is MMAO, wherein the R group of the above formula methyl or another alkyl group such as i-butyl, n-butyl, n-hexyl and others. MMAO is prepared by partial hydrolysis of a mixture of trimethyl aluminum. The selection of alkyl has an obvious effect on solubility in aliphatic hydrocarbon solvents. For example, the MMAO is selected from methylaluminoxane, i-butyl methylaluminoxane, n-butyl methylaluminoxane and n-hexyl methylaluminoxane.

Normally, the suitable solvent of MAO is an aromatic hydrocarbon solvent such as benzene, toluene, xylenes, mesitylene, cyclohexane and methylcyclohexane, while the suitable solvent of MMAO is a aliphatic hydrocarbon solvent such as n-butane, n-pentane, n-hexane, n-heptane, preferably n-hexane.

The MMAO in accordance with the present invention is deemed to be a compound containing unit represented by the following formula (II):

$$\mathrm{-[(R')AlO]}_x\mathrm{-[(R'')AlO]}_y\mathrm{-} \qquad (II)$$

wherein R' and R" are each independent alkyl group having 1 to 10 carbon atoms; and x and y are each individual integers having a sum from 5 to 10 and also having a ratio of x/y>3/1.

3. Metallocene Complex

The term "metallocene complex" as used herein refers to a complex containing at least one cyclopentadienyl ligand bonded to a transition metal selected from zirconium, titanium and hafnium.

In an embodiment, the metallocene complex in the present invention is used in the catalyst solution without a solid supported material, such as SiO, Al$_2$O$_3$, ZrO, MgCl$_2$, clay, or polystyrene.

In another embodiment, the metallocene complex of the present invention is used to contact with the MAO or the MMAO and the activating compound in the step of providing the catalyst solution for polyethylene polymerization. The metallocene complex is represented by the following formula (III):

$$\mathrm{MR^1R^2R^3R^4} \qquad (II)$$

wherein

M is a transition metal; and R$^1$, R$^2$, R$^3$ and R$^4$ are organic groups having a cycloalkadienyl skeleton or are independent selected from organic groups consisting of a cycloalkadienyl skeleton, alkyl group, alkoxy groups, aryloxy groups, alkylsilyl groups, alkylamide groups, alkylimide groups, alkylamino groups, alkylimino groups and halogen atoms.

In another embodiment, the transition metal is selected from zirconium, titanium and hafnium, preferably zirconium.

In another embodiment, the metallocene complex includes one or two ligands with cycloalkadienyl skeleton. The ligand with cycloalkadienyl skeleton is selected from, optionally alkyl substituted, cyclopentadienyl groups consisting of cyclopentadienyl, methylcyclopentadienyl, ethylcyclopentadienyl, butylcyclopentadienyl, dimethylcyclopentadienyl, pentamethylcyclo-pentadienyl, indenyl, and fluorenyl. The said cycloalkadienyl groups may be cross-linked with divalent substituted alkylene or substituted silylene.

In another embodiment, the other ligand with cycloalkadienyl skeleton is selected from the group consisting of hydrocarbon having 1 to 20 carbon atoms, alkoxy, aryloxy, alkylsilyl, amino, imino, halogen atom or hydrogen atom. The hydrocarbon group having 1 to 20 carbon atoms may be alkyl group, cycloalkyl group, aryl group, and aralkyl group. The alkoxy group may be methoxy group, ethoxy group, and butoxy group. The aryloxy group contains phenoxy group.

These functional groups may include halogen atoms or other substituents. The alkylsilyl group may be trimethylsilyl group and triethylsilyl group. The halogen atom may be fluorine, chlorine, bromine and iodine.

In a particularly preferred embodiment, the metallocene complex (including one or two ligands with cycloalkadienyl skeleton and containing zirconium as the transition metal) is selected from bis(cyclopentadienyl)zirconium monochloride monohydride,
bis(cyclopentadienyl)zirconium monobromide monohydride,
bis(cyclopentadienyl)methylzirconium hydride,
bis(cyclopentadienyl)ethylzirconium hydride,
bis(cyclopentadienyl)phenylzirconium hydride,
bis(cyclopentadienyl)benzylzirconium hydride,
bis(cyclopentadienyl)neopentylzirconium hydride,
bis(methylcyclopentadienyl)zirconium monochloride hydride,
bis(indenyl)zirconium monochloride hydride,
bis(cyclopentadienyl)zirconium dichloride,
bis(cyclopentadienyl)zirconium dibromide,
bis(cyclopentadienyl)methylzirconium monochloride,
bis(cyclopentadienyl)ethylzirconium monochloride,
bis(cyclopentadienyl)cyclohexylzirconium monochloride,
bis(cyclopentadienyl)phenylzirconium monochloride,
bis(cyclopentadienyl)benzylzirconium monochloride,
bis(methylcyclopentadienyl)zirconium dichloride,
bis(dimethylcyclopentadienyl)zirconium dichloride,
bis(1-butylcyclopentadienyl)zirconium dichloride,
bis(indenyl)zirconium dichloride, bis(indenyl)zirconium dibromide, bis(cyclopentadienyl)zirconium dimethyl,
bis(cyclopentadienyl)zirconium diphenyl, bis(cyclopentadienyl)zirconium dibenzyl,
bis(cyclopentadienyl)zirconium monomethoxymonochloride,
bis(cyclopentadienyl)zirconium monoethoxymonochloride,
bis(methylcyclopentadienyl)zirconium monoethoxymonochloride,
bis(cyclopentadienyl)zirconium monophenoxymonochloride,
bis(fluorenyl)zirconium dichloride,
ethylenebis(indenyl)dimethylzirconium,
ethylenebis(indenyl)diethylzirconium,
ethylenebis(indenyl)diphenylzirconium,
ethylenebis(indenyl)methylzirconium monochloride,
ethylenebis(indenyl)ethylzirconium monochloride,
ethylenebis(indenyl)methylzirconium monobromide,
ethylenebis(indenyl)zirconium dichloride, and
ethylenebis(indenyl)zirconium bromide.

Preparation of the Catalyst Solution

As described hereinbefore, the inventive process comprises the step of providing a catalyst solution, wherein the catalyst solution contains no additional solid support material. The solution comprises at least one activating compound, an alkylaluminoxane and a metallocene complex, wherein the molar ratio of the activating compound to aluminum comprised in the alkylaluminoxane has a significant influence on the catalytic activity.

In an embodiment, the catalyst solution is prepared (to be provided) by contacting the activating compound contacting with alkylaluminoxane in an aliphatic hydrocarbon solvent or an aromatic hydrocarbon solvent or mixture thereof followed by contacting the resultant mixture with a metallocene complex under desired conditions to obtain the homogeneous catalyst solution.

In another embodiment, the preferred solvent which is used to prepare the catalyst solution according to the present invention is selected from toluene and n-hexane.

In another embodiment, the molar ratio of the activating compound to aluminum comprised in the alkylaluminoxane is from 0.0005 to 0.20, preferably from 0.002 to 0.15 and more preferably from 0.09 to 0.12.

Preparation of Polymerized Polyethylene Wax

The preferred polymerization process in accordance with the present invention is slurry polymerization comprising the step of polymerizing ethylene by contacting the catalyst solution with ethylene, hydrogen and at least one comonomer having 3 to 10 carbon atoms under suitable process conditions to obtain polyethylene wax.

In an embodiment, the slurry polymerization process is the process in which a mixture of solid polymers and hydrocarbon solvent is reacted in at least one polymerization reactor as widely described in the open information science journal and patent literature.

The term "polymerization" as used herein refers to homopolymerization and copolymerization.

In another embodiment, a molar ratio of hydrogen to ethylene is from 0.005 to 0.05.

In another embodiment, the suitable process conditions include a temperature from 40 to 90° C. and a pressure from 1 to 12 bar and use of a hydrocarbon solvent, preferably n-hexane.

In a preferred embodiment, the polyethylene wax has a molecular weight from 500 to 20,000 g/mol, preferably 1,000 to 10,000 g/mol, measured by Gel Permeation Chromatography.

In another preferred embodiment, the polyethylene wax has a molecular weight distribution from 2 to 4 measured by Gel Permeation Chromatography.

In another preferred embodiment, the polyethylene wax has a density from 0.91 to 0.98 g/mL, preferably 0.93 to 0.98 g/mL, according to ASTM D 1505.

In another preferred embodiment, the polyethylene wax has a viscosity from 10 to 25,000 cP, preferably 10 to 1,200 cP, determined by ASTM D1968.

Measurement Standard Methods

Gel Permeation Chromatography (GPC)

8 mg of sample was dissolved in 8 ml of 1,2,4-trichlorobenzene at 160° C. for 90 min. Then, 200 µl of the sample solution was injected into the high temperature GPC with IR5, an infrared detector (Polymer Char, Spain) with flow rate of 0.5 ml/min at 145° C. in column zone and 160° C. in detector zone. The data was processed by GPC One® software, Polymer Char, Spain.

Molecular weight and Polydispersity index (PDI): The weight average molecular weight (Mw), the number average molecular weight (Mn), and the molecular weight distribution (Mw/Mn) in g/mol were analyzed by gel permeation chromatography (GPC). Polydispersity index was calculated by Mw/Mn.

Density: Density of polyethylene was measured by observing the level to which a pellet sinks in a liquid column gradient tube, in comparison with standards of known density. This method is determination of the solid plastic after annealing at 120° C. follow ASTM D 1505.

Viscosity: Viscosity of polyethylene wax was measured according to ASTM D 1968 and indicated in centipoise (cP) that determines the physical property of polyethylene wax and may determine the utility of the wax, as well as being a significant quality control test under testing condition using the Brookfield LVT or LVF viscometer and thermosel system.

Scanning Electron Microscope

Jeol SEM-6610LA SEM was used to characterize and investigate the morphology of polymer. The samples were coated with gold particles by ion sputtering device to provide electrical contact to the specimen before analyzing.

EXAMPLES

The present invention is described in the following in detail with reference to several examples and comparative examples. However, the present invention is not limited to the examples. In the processes described below, each reaction was conducted in an inert atmosphere and each solvent was dehydrated before use.

Example 1

(1) Preparation of Catalyst A 1.48 mmol MMAO-3A solution (MAO, purchased from Tosoh Finechem Corporation; Al 5.7% wt; 15% wt MAO in hexane solution) was diluted with 9 mL of dried n-hexane. After that, 0.03 mmol Bis(butylcyclopentadienyl)zirconium (IV)$Cl_2$ (purchased from Strem Chemicals Inc.) was added to the MMAO-3A solution to obtain the catalyst solution.

Example 2

(1) Preparation of Catalyst B-1

1.48 mmol MMAO-3A solution (MAO, purchased from Tosoh Finechem Corporation; Al 5.7% wt; 15% wt MAO in hexane solution) was diluted with 9 mL of dried n-hexane and mixed with 0.0018 mmol 2,3,4,5,6-pentafluorophenol (purchased from Sigma-Aldrich). After that, 0.03 mmol Bis(butylcyclopentadienyl)zirconium(IV)Cl$_2$ (purchased from Strem Chemicals Inc.) was added to the mixture to obtain the catalyst solution.

(2) Preparation of Catalyst B-2

1.48 mmol MMAO-3A solution (MAO, purchased from Tosoh Finechem Corporation; Al 5.7% wt; 15% wt MAO in hexane solution) was diluted with 9 mL of dried n-hexane and mixed with 0.07 mmol 2,3,4,5,6-pentafluorophenol (purchased from Sigma-Aldrich). After that, 0.03 mmol Bis(butylcyclopentadienyl)zirconium(IV)Cl$_2$ (purchased from Strem Chemicals Inc.) was added to the mixture to obtain the catalyst solution.

(3) Preparation of Catalyst B-3

1.48 mmol MMAO-3A solution (MAO, purchased from Tosoh Finechem Corporation; Al 5.7% wt; 15% wt MAO in hexane solution) was diluted with 9 mL of dried n-hexane and mixed with 0.11 mmol 2,3,4,5,6-pentafluorophenol (purchased from Sigma-Aldrich). After that, 0.03 mmol Bis(butylcyclopentadienyl)zirconium(IV)Cl$_2$ (purchased from Strem Chemicals Inc.) was added to the mixture to obtain the catalyst solution.

(4) Preparation of Catalyst B-4

1.48 mmol MMAO-3A solution (MAO, purchased from Tosoh Finechem Corporation; Al 5.7% wt; 15% wt MAO in hexane solution) was diluted with 9 mL of dried n-hexane and mixed with 0.15 mmol 2,3,4,5,6-pentafluorophenol (purchased from Sigma-Aldrich). After that, 0.03 mmol Bis(butylcyclopentadienyl)zirconium(IV)Cl$_2$ (purchased from Strem Chemicals Inc.) was added to the mixture to obtain the catalyst solution.

(5) Preparation of Catalyst B-5

1.48 mmol MMAO-3A solution (MAO, purchased from Tosoh Finechem Corporation; Al 5.7% wt; 15% wt MAO in hexane solution) was diluted with 9 mL of dried n-hexane and mixed with 0.18 mmol 2,3,4,5,6-pentafluorophenol (purchased from Sigma-Aldrich). After that, 0.03 mmol Bis(butylcyclopentadienyl)zirconium(IV)Cl$_2$ (purchased from Strem Chemicals Inc.) was added to the mixture to obtain the catalyst solution.

Example 3

Ethylene Polymerization

The polymerization process of polyethylene wax was provided in a 2-liter stainless steel autoclave reactor. 800 mL of dried n-hexane was added followed by the addition of the catalyst solution into a polymerization reactor. A mixture of hydrogen and ethylene gases with a ratio of 0.05 mol/mol was introduced and started the polymerization with an ethylene pressure of 8.5 barg at 85° C. for 1 hour. The solid product was collected by filtration and dried under vacuum to obtain a free flow polymer.

Comparative Example 1

The polymerization was conducted by the same procedure as Example 3 using Catalyst A. The result was shown in Table 1.

Comparative Example 2

The polymerization was conducted by the same procedure as Example 3 using Catalyst B-1. The result was shown in Table 1.

Comparative Example 3

The polymerization was conducted by the same procedure as Example 3 using Catalyst B-2. The result was shown in Table 1.

Comparative Example 4

The polymerization was conducted by the same procedure as Example 3 using Catalyst B-3. The result was shown in Table 1.

Comparative Example 5

The polymerization was conducted by the same procedure as Example 3 using Catalyst B-4. The result was shown in Table 1.

Comparative Example 6

The polymerization was conducted by the same procedure as Example 3 using Catalyst B-5. The result was shown in Table 1.

TABLE 1

| Example | Catalyst Name | $M_1:Al_{MAO}$ (mol/mol) | Activity (KgPE/molZr · h) | Viscosity at 140° C. (cP) | Density (g/mL) | Mw (g/mol) | Mn (g/mol) | Mw/Mn |
|---|---|---|---|---|---|---|---|---|
| Comparative Example 1 | Catalyst A | 0 | 3.969 | 25.3 | 0.9624 | 1,670 | 808 | 2.07 |
| Comparative Example 2 | Catalyst B-1 | 0.0015 | 3.585 | 27.0 | 0.9635 | 1,740 | 858 | 2.03 |
| Comparative Example 3 | Catalyst B-2 | 0.06 | 7.376 | 24.7 | 0.9622 | 1,692 | 790 | 2.14 |
| Comparative Example 4 | Catalyst B-3 | 0.09 | 7.241 | 24.0 | 0.9617 | 1,651 | 760 | 2.17 |
| Comparative Example 5 | Catalyst B-4 | 0.12 | 8.488 | 23.0 | 0.9614 | 1,672 | 732 | 2.28 |
| Comparative Example 6 | Catalyst B-5 | 0.15 | 6.298 | 25.8 | 0.9623 | 1,459 | 607 | 2.40 |

$M_1$: 2,3,4,5,6-pentafluorophenol

The polymerization results according to Comparative Example 2 to 6 show the effect of the additional variation of the molar ratio of 2,3,4,5,6-pentafluorophenol to aluminum comprised in the alkylaluminoxane compared with Comparative Example 3 showing the absence of activating compound.

In an embodiment, Comparative Example 3, 4, 5 and 6 having a specific molar ratio of 2,3,4,5,6-pentafluorophenol to aluminum comprised in the alkylaluminoxane result in a higher performance of polymerization activity than Comparative Example 3. Comparative Example 2 has a molar ratio of 2,3,4,5,6-pentafluorophenol to aluminum comprised in the alkylaluminoxane of 0.0015 and shows a lower performance of polymerization activity than Comparative Example 3, 4, 5, and 6.

Example 4

(1) Preparation of Catalyst C-1

1.48 mmol MMAO-3A solution (MAO, purchased from Tosoh Finechem Corporation; Al 5.7% wt; 15% wt MAO in hexane solution) was diluted with 9 mL of dried n-hexane and mixed with 0.006 mmol 4-fluorophenol (purchased from Sigma-Aldrich). After that 0.03 mmol Bis(butylcyclopentadienyl)zirconium(IV)Cl$_2$ (purchased from Strem Chemicals Inc.) was added to the mixture to obtain the catalyst solution.

(2) Preparation of Catalyst C-2

1.48 mmol MMAO-3A solution (MAO, purchased from Tosoh Finechem Corporation; Al 5.7% wt; 15% wt MAO in hexane solution) was diluted with 9 mL of dried n-hexane and mixed with 0.012 mmol 4-fluorophenol (purchased from Sigma-Aldrich). After that 0.03 mmol Bis(butylcyclopentadienyl)zirconium(IV)Cl$_2$ (purchased from Strem Chemicals Inc.) was added to the mixture to obtain the catalyst solution.

(3) Preparation of Catalyst C-3

1.48 mmol MMAO-3A hexane solution (MAO, purchased from Tosoh Finechem Corporation; Al 5.7% wt; 15% wt MAO in hexane solution) was diluted with 9 mL of dried n-hexane and mixed with 0.07 mmol 4-fluorophenol (purchased from Sigma-Aldrich). After that 0.03 mmol Bis(butylcyclopentadienyl)zirconium(IV)Cl$_2$ (purchased from Strem Chemicals Inc.) was added to the mixture to obtain the catalyst solution.

(4) Preparation of Catalyst C-4

1.48 mmol MMAO-3A hexane solution (MAO, purchased from Tosoh Finechem Corporation; Al 5.7% wt; 15% wt MAO in hexane solution) was diluted with 9 mL of dried n-hexane and mixed with 0.1 mmol 4-fluorophenol (purchased from Sigma-Aldrich). After that 0.03 mmol Bis(butylcyclopentadienyl)zirconium(IV)Cl$_2$ (purchased from Strem Chemicals Inc.) was added to the mixture to obtain the catalyst solution.

Comparative Example 7

The polymerization was conducted by the same procedure as Example 3 using Catalyst C-1. The result was shown in Table 2.

Comparative Example 8

The polymerization was conducted by the same procedure as Example 3 using Catalyst C-2. The result was shown in Table 2.

Comparative Example 9

The polymerization was conducted by the same procedure as Example 3 using Catalyst C-3. The result is shown in Table 2.

Comparative Example 10

The polymerization was conducted by the same procedure as Example 3 using Catalyst C-4. The result was shown in Table 2.

TABLE 2

| Example | Catalyst Name | M$_2$:Al$_{(MAO)}$ (mol/mol) | Activity (KgPE/molZr · h) | Viscosity at 140° C. (cP) | Density (g/mL) | Mw (g/mol) | Mn (g/mol) | Mw/Mn |
|---|---|---|---|---|---|---|---|---|
| Comparative Example 1 | Catalyst A | 0 | 3.969 | 25.3 | 0.9624 | 1,670 | 808 | 2.07 |
| Comparative Example 7 | Catalyst C-1 | 0.005 | 4.595 | 117 | 0.9730 | 2,607 | 1,066 | 2.45 |
| Comparative Example 8 | Catalyst C-2 | 0.01 | 4.917 | 94 | 0.9737 | 2,652 | 1,068 | 2.48 |
| Comparative Example 9 | Catalyst C-3 | 0.06 | 3.491 | 189 | 0.9722 | 2,644 | 1,048 | 2.52 |
| Comparative Example 10 | Catalyst C-4 | 0.09 | 2.414 | 143 | 0.9690 | 2,716 | 1,146 | 2.37 |

M$_2$: 4-fluorophenol

The polymerization results according to Comparative Example 7 to 10 show the effect of the additional variation of the molar ratio of 4-fluorophenol to aluminum comprised in the alkylaluminoxane compared with Comparative Example 1 the absence of activating compound.

In an embodiment, Comparative Example 7 and 8 having a molar ratio of 4-fluorophenol to aluminum comprised in the alkylaluminoxane are from 0.005 to 0.01 and result in an enhancement of polymerization activity in comparison with Comparative Example 1. Comparative Example 9 and 10 have a molar ratio of 4-fluorophenol to aluminum comprised in the alkylaluminoxane which is higher than that of Comparative Example 7 and 8 representing a lower performance of polymerization activity.

Example 5

(1) Preparation of Catalyst D-1

1.48 mmol MMAO-3A solution (MAO, purchased from Tosoh Finechem Corporation; Al 5.7% wt; 15% wt MAO in hexane solution) was diluted with 9 mL of dried n-hexane and mixed with 0.002 mmol phenol (purchased from Sigma-Aldrich). After that, 0.03 mmol Bis(butylcyclopentadienyl)zirconium(IV)Cl$_2$ (purchased from Strem Chemicals Inc.) was added to the mixture to obtain the catalyst solution.

(2) Preparation of Catalyst D-2

1.48 mmol MMAO-3A solution (MAO, purchased from Tosoh Finechem Corporation; Al 5.7% wt; 15% wt MAO in hexane solution) was diluted with 9 mL of dried n-hexane and mixed with 0.004 mmol phenol (purchased from Sigma-Aldrich). After that, 0.03 mmol Bis(butylcyclopentadienyl)zirconium(IV)Cl$_2$ (purchased from Strem Chemicals Inc.) was added to the mixture to obtain the catalyst solution.

(3) Preparation of Catalyst D-3

1.48 mmol MMAO-3A solution (MAO, purchased from Tosoh Finechem Corporation; Al 5.7% wt; 15% wt MAO in hexane solution) was diluted with 9 mL of dried n-hexane and mixed with 0.008 mmol phenol (purchased from Sigma-Aldrich). After that, 0.03 mmol Bis(butylcyclopentadienyl)zirconium(IV)Cl$_2$ (purchased from Strem Chemicals Inc.) was added to the mixture to obtain the catalyst solution.

(4) Preparation of Catalyst D-4

1.48 mmol MMAO-3A hexane solution (MAO, purchased from Tosoh Finechem Corporation; Al 5.7% wt; 15% wt MAO in hexane solution) was diluted with 9 mL of dried n-hexane and mixed with 0.016 mmol phenol (purchased from Sigma-Aldrich). After that, 0.03 mmol Bis(butylcyclopentadienyl)zirconium(IV)Cl$_2$ (purchased from Strem Chemicals Inc.) was added to the mixture to obtain the catalyst solution.

(5) Preparation of Catalyst D-5

1.48 mmol MMAO-3A hexane solution (MAO, purchased from Tosoh Finechem Corporation; Al 5.7% wt; 15% wt MAO in hexane solution) was diluted with 9 mL of dried n-hexane and mixed with 0.032 mmol phenol (purchased from Sigma-Aldrich). After that, 0.03 mmol Bis(butylcyclopentadienyl)zirconium(IV)Cl$_2$ (purchased from Strem Chemicals Inc.) was added to the mixture to obtain the catalyst solution.

(6) Preparation of Catalyst D-6

1.48 mmol MMAO-3A hexane solution (MAO, purchased from Tosoh Finechem Corporation; Al 5.7% wt; 15% wt MAO in hexane solution) was diluted with 9 mL of dried n-hexane and mixed with 0.064 mmol phenol (purchased from Sigma-Aldrich). After that, 0.03 mmol Bis(butylcyclopentadienyl)zirconium(IV)Cl$_2$ (purchased from Strem Chemicals Inc.) was added to the mixture to obtain the catalyst solution.

Comparative Example 11

The polymerization was conducted by in the same procedure as Example 3 using Catalyst D-1. The result was shown in Table 3.

Comparative Example 12

The polymerization was conducted by in the same procedure as Example 3 using Catalyst D-2. The result was shown in Table 3.

Comparative Example 13

The polymerization was conducted by in the same procedure as Example 3 using Catalyst D-3. The result was shown in Table 3.

Comparative Example 14

The polymerization was conducted by in the same procedure as Example 3 using Catalyst D-4. The result was shown in Table 3.

Comparative Example 15

The polymerization was conducted by in the same procedure as Example 3 using Catalyst D-5. The result was shown in Table 3.

Comparative Example 16

The polymerization was conducted by in the same procedure as Example 3 using Catalyst D-6. The result was shown in Table 3.

TABLE 3

| Example | Catalyst Name | M$_3$:Al$_{(MAO)}$ (mol/mol) | Activity (KgPE/molZr · h) | Viscosity at 140° C. (cP) | Density (g/mL) | Mw (g/mol) | Mn (g/mol) | Mw/Mn |
|---|---|---|---|---|---|---|---|---|
| Comparative Example 1 | Catalyst A | 0 | 3.969 | 25.3 | 0.9624 | 1,670 | 808 | 2.07 |
| Comparative Example 11 | Catalyst D-1 | 0.0015 | 2.665 | 249 | 0.9756 | 3,251 | 1,320 | 2.46 |
| Comparative Example 12 | Catalyst D-2 | 0.0031 | 4.673 | 136 | 0.9720 | 3,422 | 1,398 | 2.45 |
| Comparative Example 13 | Catalyst D-3 | 0.0062 | 4.179 | 134 | 0.9707 | 2,880 | 1,153 | 2.50 |
| Comparative Example 14 | Catalyst D-4 | 0.0125 | 4.621 | 103 | 0.9737 | 2,657 | 1,112 | 2.39 |
| Comparative Example 15 | Catalyst D-5 | 0.025 | 3.737 | 153 | 0.9745 | 3,005 | 1,160 | 2.59 |
| Comparative Example 16 | Catalyst D-6 | 0.05 | 2.240 | 168 | 0.9707 | 2,707 | 1,050 | 2.58 |

M$_3$: phenol

The polymerization results according to Comparative Example 11 to 16 show the effect of the additional variation of the molar ratio of phenol to aluminum comprised in the alkylaluminoxane compared with Comparative Example 1 showing the absence of activating compound.

In an embodiment, Comparative Example 12 to 14 have a molar ratio of phenol to aluminum comprised in the alkylaluminoxane from 0.0031 to 0.0125 resulting in a higher performance of polymerization activity in comparison with Comparative Example 1. While Comparative Example 11, 15 and 16 have a molar ratio of phenol to aluminum comprised in the alkylaluminoxane in the lower and upper ratio of Comparative Example 12 to 14 showing a lower performance of polymerization activity.

Example 6

(1) Preparation of Catalyst E-1

1.48 mmol MMAO-3A hexane solution (MAO, purchased from Tosoh Finechem Corporation; Al 5.7% wt; 15% wt MAO in hexane solution) was diluted with 9 mL of dried n-hexane and mixed with 0.0006 mmol 3,5-Bis(trifluoromethane)phenol (purchased from TCI). After that 0.03 mmol Bis(butylcyclopentadienyl)zirconium(IV)Cl$_2$ (purchased from Strem Chemicals Inc.) was added to the mixture to obtain the catalyst solution.

(2) Preparation of Catalyst E-2

1.48 mmol MMAO-3A hexane solution (MAO, purchased from Tosoh Finechem Corporation; Al 5.7% wt; 15% wt MAO in hexane solution) was diluted with 9 mL of dried n-hexane and mixed with 0.002 mmol 3,5-Bis(trifluoromethane)phenol (purchased from TCI). Then, 0.03 mmol Bis(butylcyclopentadienyl)zirconium(IV)Cl$_2$ (purchased from Strem Chemicals Inc.) was added to the mixture to obtain the catalyst solution.

(3) Preparation of Catalyst E-3

1.48 mmol MMAO-3A hexane solution (MAO, purchased from Tosoh Finechem Corporation; Al 5.7% wt; 15% wt MAO in hexane solution) was diluted with 9 mL of dried n-hexane and mixed with 0.006 mmol of 3,5-Bis(trifluoromethane)phenol (purchased from TCI). After that 0.03 mmol Bis(butylcyclopentadienyl)zirconium(IV)Cl$_2$ (purchased from Strem Chemicals Inc.) was added to the mixture to obtain the catalyst solution.

(4) Preparation of Catalyst E-4

1.48 mmol of MMAO-3A hexane solution (MAO, purchased from Tosoh Finechem Corporation; Al 5.7% wt; 15% wt MAO in hexane solution) was diluted with 9 mL of dried n-hexane and mixed with 0.012 mmol 3,5-Bis(trifluoromethane)phenol (purchased from TCI). After that 0.03 mmol Bis(butylcyclopentadienyl)zirconium(IV)Cl$_2$ (purchased from Strem Chemicals Inc.) was added to the mixture to obtain the catalyst solution.

(5) Preparation of Catalyst E-5

1.48 mmol MMAO-3A hexane solution (MAO, purchased from Tosoh Finechem Corporation; Al 5.7% wt; 15% wt MAO in hexane solution) was diluted with 9 mL of dried n-hexane and mixed with 0.073 mmol 3,5-Bis(trifluoromethane)phenol (purchased from TCI). After that 0.03 mmol Bis(butylcyclopentadienyl)zirconium(IV)Cl$_2$ (purchased from Strem Chemicals Inc.) was added to the mixture to obtain the catalyst solution.

Comparative Example 17

The polymerization was conducted by the same procedure as Example 3 using Catalyst E-1. The result was shown in Table 4.

Comparative Example 18

The polymerization was conducted by the same procedure as Example 3 using Catalyst E-2. The result was shown in Table 4.

Comparative Example 19

The polymerization was conducted by the same procedure as Example 3 using Catalyst E-3. The result was shown in Table 4.

Comparative Example 20

The polymerization was conducted by the same procedure as Example 3 using Catalyst E-4. The result was shown in Table 4.

TABLE 4

| Example | Catalyst Name | $M_4:Al_{(MAO)}$ (mol/mol) | Activity (KgPE/molZr · h) | Viscosity at 140° C. (cP) | Density (g/mL) | Mw (g/mol) | Mn (g/mol) | Mw/Mn |
|---|---|---|---|---|---|---|---|---|
| Comparative Example 1 | Catalyst A | 0 | 3.969 | 25.3 | 0.9624 | 1,670 | 808 | 2.07 |
| Comparative Example 17 | Catalyst E-1 | 0.0005 | 4.055 | 84 | 0.9735 | 2,778 | 1,135 | 2.45 |
| Comparative Example 18 | Catalyst E-2 | 0.002 | 4.490 | 140 | 0.9738 | 3,250 | 1,378 | 2.55 |
| Comparative Example 19 | Catalyst E-3 | 0.005 | 3.952 | 103 | 0.9725 | 2,604 | 979 | 2.66 |
| Comparative Example 20 | Catalyst E-4 | 0.01 | 3.687 | 215 | 0.9717 | 4,119 | 1,493 | 2.76 |

$M_4$: 3,5-Bis(trifluoromethane)phenol

The polymerization results according to Comparative Example 17 to 20 show the effect of the additional variation of the molar ratio of 3,5-Bis(trifluoromethane)phenol to aluminum comprised in the alkylaluminoxane compared with Comparative Example 1 showing the absence of activating compound.

In an embodiment, Comparative Example 17 and 18 have a molar ratio of 3,5-Bis(trifluoromethane)phenol to aluminum comprised in the alkylaluminoxane from 0.0005 to 0.002 resulting in the enhancement of polymerization activity in comparison with Comparative Example 1. Comparative Examples 19 and 20 have a molar ratio of 3,5-Bis(trifluoromethane)phenol to aluminum comprised in the alkylaluminoxane which higher than that of Comparative Example 17 and 18 showing a lower performance of polymerization activity.

Example 7

(1) Preparation of Catalyst F-1

1.48 mmol MMAO-3A solution (MAO, purchased from Tosoh Finechem Corporation; Al 5.7% wt; 15% wt MAO in hexane solution) was diluted with 9 mL of dried n-hexane and mixed with 0.03 mmol 2,6-bis(tert-butyl)-4-methylphenol (purchased from Sigma-Aldrich). After that 0.03 mmol Bis(butylcyclopentadienyl)zirconium(IV)Cl$_2$ (purchased from Strem Chemicals Inc.) was added to the mixture to obtain the catalyst solution.

(2) Preparation of Catalyst F-2

1.48 mmol MMAO-3A solution (MAO, purchased from Tosoh Finechem Corporation; Al 5.7% wt; 15% wt MAO in hexane solution) was diluted with 9 mL of dried n-hexane and mixed with 0.06 mmol 2,6-bis(tert-butyl)-4-methylphenol (purchased from Sigma-Aldrich). After that 0.03 mmol Bis(butylcyclopentadienyl)zirconium(IV)Cl$_2$ (purchased from Strem Chemicals Inc.) was added to the mixture to obtain the catalyst solution.

(3) Preparation of Catalyst F-3

1.48 mmol MMAO-3A solution (MAO, purchased from Tosoh Finechem Corporation; Al 5.7% wt; 15% wt MAO in hexane solution) was diluted with 9 mL of dried n-hexane and mixed with 0.12 mmol 2,6-bis(tert-butyl)-4-methylphenol (purchased from Sigma-Aldrich). After that 0.03 mmol Bis(butylcyclopentadienyl)zirconium(IV)Cl$_2$ (purchased from Strem Chemicals Inc.) was added to the mixture to obtain the catalyst solution.

(4) Preparation of Catalyst F-4

1.48 mmol MMAO-3A solution (MAO, purchased from Tosoh Finechem Corporation; Al 5.7% wt; 15% wt MAO in hexane solution) was diluted with 9 mL of dried n-hexane and mixed with 0.15 mmol 2,6-bis(tert-butyl)-4-methylphenol (purchased from Sigma-Aldrich). Then, 0.03 mmol of Bis(butylcyclopentadienyl)zirconium(IV)Cl$_2$ (purchased from Strem Chemicals Inc.) was added to the mixture to obtain the catalyst solution.

Comparative Example 21

The polymerization was conducted by the same procedure as Example 3 using Catalyst F-1. The result was shown in Table 5.

Comparative Example 22

The polymerization was conducted by the same procedure as Example 3 using Catalyst F-2. The result was shown in Table 5.

Comparative Example 23

The polymerization was conducted by the same procedure as Example 3 using Catalyst F-3. The result was shown in Table 5.

Comparative Example 24

The polymerization was conducted by the same procedure as Example 3 using Catalyst F-4. The result was shown in Table 5.

Comparative Example 22 and 23 showing a lower performance of polymerization activity.

Example 8

(1) Preparation of Catalyst G-1

1.48 mmol MMAO-3A solution (MAO, purchased from Tosoh Finechem Corporation; Al 5.7% wt; 15% wt MAO in hexane solution) was diluted with 9 mL of dried n-hexane and mixed with 0.03 mmol 2,2,2-trifluoroethanol (purchased from Sigma-Aldrich). After that 0.03 mmol Bis(butylcyclopentadienyl)zirconium(IV)Cl$_2$ (purchased from Strem Chemicals Inc.) was added to the mixture to obtain the catalyst solution.

(2) Preparation of Catalyst G-2

1.48 mmol MMAO-3A solution (MAO, purchased from Tosoh Finechem Corporation; Al 5.7% wt; 15% wt MAO in hexane solution) was diluted with 9 mL of dried n-hexane and mixed with 0.07 mmol 2,2,2-trifluoroethanol (purchased from Sigma-Aldrich). After that 0.03 mmol Bis(butylcyclopentadienyl)zirconium(IV)Cl$_2$ (purchased from Strem Chemicals Inc.) was added to the mixture to obtain the catalyst solution.

(3) Preparation of Catalyst G-3

1.48 mmol MMAO-3A solution (MAO, purchased from Tosoh Finechem Corporation; Al 5.7% wt; 15% wt MAO in hexane solution) was diluted with 9 mL of dried n-hexane and mixed with 0.12 mmol 2,2,2-trifluoroethanol (purchased from Sigma-Aldrich). After that 0.03 mmol Bis(butylcyclopentadienyl)zirconium(IV)Cl$_2$ (purchased from Strem Chemicals Inc.) was added to the mixture to obtain the catalyst solution.

TABLE 5

| Example | Catalyst Name | M$_5$:Al$_{(MAO)}$ (mol/mol) | Activity (KgPE/molZr · h) | Viscosity at 140° C. (cP) | Density (g/mL) | Mw (g/mol) | Mn (g/mol) | Mw/Mn |
|---|---|---|---|---|---|---|---|---|
| Comparative Example 1 | Catalyst A | 0 | 3.969 | 25.3 | 0.9624 | 1,670 | 808 | 2.07 |
| Comparative Example 21 | Catalyst F-1 | 0.024 | 3.165 | 169 | 0.9734 | 3,246 | 1,321 | 2.46 |
| Comparative Example 22 | Catalyst F-2 | 0.048 | 4.611 | 152 | 0.9729 | 2,650 | 1,058 | 2.51 |
| Comparative Example 23 | Catalyst F-3 | 0.096 | 4.975 | 155 | 0.9754 | 3,473 | 1,497 | 2.32 |
| Comparative Example 24 | Catalyst F-4 | 0.12 | 2.479 | 109 | 0.9716 | 2,691 | 1,189 | 2.26 |

M$_5$: 2,6-bis(tert-butyl)-4-methylphenol

The polymerization results according to Comparative Example 21 to 24 show the effect of the additional variation of the molar ratio of 2,6-bis(tert-butyl)-4-methylphenol to aluminum comprised in the alkylaluminoxane compared with Comparative Example 1 showing the absence of activating compound.

In an embodiment, Comparative Example 22 and 23 have a molar ratio of 2,6-bis(tert-butyl)-4-methylphenol to aluminum comprised in the alkylaluminoxane from 0.048 to 0.096 resulting in a higher performance of polymerization activity in comparison with Comparative Example 1. Comparative Example 21 and 24 have a molar ratio of 2,6-bis(tert-butyl)-4-methylphenol to aluminum comprised in the alkylaluminoxane which lower and upper than ratio of (4) Preparation of Catalyst G-4

1.48 mmol MMAO-3A solution (MAO, purchased from Tosoh Finechem Corporation; Al 5.7% wt; 15% wt MAO in hexane solution) was diluted with 9 mL of dried n-hexane and mixed with 0.24 mmol 2,2,2-trifluoroethanol (purchased from Sigma-Aldrich). After that 0.03 mmol Bis(butylcyclopentadienyl)zirconium(IV)Cl$_2$ (purchased from Strem Chemicals Inc.) was added to the mixture to obtain the catalyst solution.

Comparative Example 25

The polymerization was conducted by the same procedure as Example 3 using Catalyst G-1. The result was shown in Table 6.

Comparative Example 26

The polymerization was conducted by the same procedure as Example 3 using Catalyst G-2. The result was shown in Table 6.

Comparative Example 27

The polymerization was conducted by the same procedure as Example 3 using Catalyst G-3. The result was shown in Table 6.

Comparative Example 28

The polymerization was conducted by the same procedure as Example 3 using Catalyst G-4. The result was shown in Table 6.

TABLE 6

| Example | Catalyst Name | $M_6$:$Al_{(MAO)}$ (mol/mol) | Activity (KgPE/molZr · h) | Viscosity at 140° C. (cP) | Density (g/mL) | Mw (g/mol) | Mn (g/mol) | Mw/Mn |
|---|---|---|---|---|---|---|---|---|
| Comparative Example 1 | Catalyst A | 0 | 3.969 | 25.3 | 0.9624 | 1,670 | 808 | 2.07 |
| Comparative Example 25 | Catalyst G-1 | 0.025 | 3.937 | 114 | 0.9707 | 2,960 | 1,080 | 2.74 |
| Comparative Example 26 | Catalyst G-2 | 0.059 | 5.089 | 196 | 0.9730 | 2,695 | 1,061 | 2.54 |
| Comparative Example 27 | Catalyst G-3 | 0.098 | 4.786 | 128 | 0.9715 | 2,743 | 1,105 | 2.48 |
| Comparative Example 28 | Catalyst G-4 | 0.2 | 0.786 | 131 | 0.9786 | 3,305 | 1,369 | 2.41 |

$M_6$: 2,2,2-trifluoroethanol

The polymerization results according to Comparative Example 25 to 28 show the effect of the additional variation of the molar ratio of 2,2,2-trifluoroethanol to aluminum comprised in the alkylaluminoxane compared with Comparative Example 1 showing the absence of activating compound.

In an embodiment, Comparative Example 25 shows a close performance of polymerization activity with Comparative Example 1; however, the other properties as shown in Table 6 are higher. Comparative Example 26 and 27 have a molar ratio of 2,2,2-trifluoroethanol to aluminum comprised in the alkylaluminoxane are from 0.059 to 0.098 resulting in the enhancement of polymerization activity in comparison with Comparative Example 1. Comparative Example 28 represents a lower polymerization activity than Comparative Example 25 to 27, wherein the molar ratio of 2,2,2-trifluoroethanol to aluminum comprised in the alkylaluminoxane is 0.2.

Example 9

(1) Preparation of Catalyst B4-1

1.48 mmol MMAO-3A solution (MAO, purchased from Tosoh Finechem Corporation; Al 5.7% wt; 15% wt MAO in hexane solution) was diluted with 9 mL of dried n-hexane and mixed with 0.15 mmol 2,3,4,5,6-pentafluorophenol (supplied by Sigma Aldrich) to obtain MMAO-3A solution followed by the addition of 0.05 mmol Bis(butylcyclopentadienyl)zirconium(IV)Cl$_2$ (supplied by Strem) to the activated MMAO-3A solution to the catalyst solution obtained.

(2) Preparation of Catalyst B4-2

1.48 mmol MMAO-3A solution (MAO, made by Tosoh Finechem; Al 5.7% wt; 15% wt MAO in hexane solution) was diluted with 9 mL of dried n-hexane. After that, 0.15 mmol 2,3,4,5,6-pentafluorophenol (purchased from Sigma-Aldrich) followed by the addition of 0.012 mmol Bis(butylcyclopentadienyl)zirconium(IV)Cl$_2$ (purchased from Strem Chemicals Inc.) to the activated MMAO-3A solution to obtain the catalyst solution.

(3) Preparation of Catalyst B4-3

1.48 mmol MMAO-3A solution (MAO, made by Tosoh Finechem; Al 5.7% wt; 15% wt MAO in hexane solution) was diluted with 9 mL of dried n-hexane. After that, 0.15 mmol 2,3,4,5,6-pentafluorophenol (purchased from Sigma-Aldrich) followed by the addition of 0.006 mmol Bis(butylcyclopentadienyl)zirconium(IV)Cl$_2$ (purchased from Strem Chemicals Inc.) to the activated MMAO-3A solution to obtain the catalyst solution.

Comparative Example 29

The polymerization was conducted by the same procedure as Example 3 using Catalyst B4-1. The result was shown in Table 7.

Comparative Example 30

The polymerization was conducted by the same procedure as Example 3 using Catalyst B4-2. The result was shown in Table 7.

Comparative Example 31

The polymerization was conducted by the same procedure as Example 3 using Catalyst B4-3. The result was shown in Table 7.

TABLE 7

| Example | Catalyst Name | $M_7:Al_{(MAO)}$ (mol/mol) | $Al_{(MAO)}:Zr_{(MET)}$ | Activity (KgPE/molZr · h) | Viscosity at 140° C. (cP) | Density (g/mL) | Mw (g/mol) | Mn (g/mol) | Mw/Mn |
|---|---|---|---|---|---|---|---|---|---|
| Comparative Example 5 | Catalyst B4 | 0.12 | 42 | 8.488 | 23.0 | 0.9614 | 1,672 | 732 | 2.28 |
| Comparative Example 29 | Catalyst B4-1 | 0.12 | 25 | 3.596 | 68 | 0.9714 | 2,490 | 1,153 | 2.16 |
| Comparative Example 30 | Catalyst B4-2 | 0.12 | 100 | 21.964 | 135 | 0.9727 | 3,403 | 1,330 | 2.56 |
| Comparative Example 31 | Catalyst B4-3 | 0.12 | 200 | 7.208 | 281 | 0.9737 | 3,506 | 1,397 | 2.51 |

$M_7$: 2,3,4,5,6-pentafluorophenol and Bis(butylcyclopentadienyl)zirconium(IV)Cl$_2$ with $Al_{(MAO)}:Zr_{(MET)}$ variation MET: Metallocene complex The polymerization results according to Comparative Example 29 to 31 show the effect of the additional variation of the molar ratio of aluminum comprised in the alkylaluminoxane to zirconium comprised in a metallocene complex when the molar ratio of activating compound mixture to aluminum comprised in the alkylaluminoxane is 0.12.

In an embodiment, the activating compound mixture comprises 2,3,4,5,6-pentafluorophenol and Bis(butylcyclopentadienyl)zirconium(IV)Cl$_2$.

In another embodiment, Comparative Example 30 having a specific molar ratio of aluminum comprised in the alkylaluminoxane to zirconium comprised in the metallocene complex results in the highest performance of polymerization activity in comparison with Comparative Example 29 and 31, including also Comparative Example 5.

Example 10

Preparation of Catalyst H-1

1.48 mmol MMAO-3A solution (MAO, purchased from Tosoh Finechem Corporation; Al 5.7% wt; 15% wt MAO in hexane solution) was diluted with 9 mL of dried n-hexane and mixed with 0.03 mmol of 2,3,4,5,6-pentafluorophenol (purchased from Sigma-Aldrich) and 0.12 mmol 2,6-bis(tert-butyl)-4-methylphenol (purchased from Sigma-Aldrich). After that, 0.03 mmol Bis(butylcyclopentadienyl)zirconium(IV)Cl$_2$ (purchased from Strem Chemicals Inc.) was added to the mixture to obtain the catalyst solution.

Comparative Example 32

The polymerization was conducted by the same procedure as Example 3 using Catalyst H-1. The result was shown in Table 8.

In an embodiment, the molar ratio of activating compound mixture to aluminum comprised in the alkylaluminoxane is 0.12.

In another embodiment, the activating compound mixture comprises 2,3,4,5,6-pentafluorophenol and 2,6-bis(tert-butyl)-4-methylphenol.

In another embodiment, Comparative Example 32 having a specific molar ratio of activating compound mixture to aluminum comprised in the alkylaluminoxane results in a higher performance of polymerization activity in comparison with Comparative Example 1.

Example 11

(1) Ethylene/1-Butene Copolymerization

The polymerization process of polyethylene wax was conducted in a 2-liter stainless steel autoclave reactor. 800 mL of dried n-hexane was added followed by the addition of 0.2 mmol/L tri-isobutyl aluminum in n-hexane solution and 20 g of 1-butene was also added in this step. After that, the catalyst solution was added in the polymerization reactor. A mixture of hydrogen and ethylene gases with a ratio of 0.05 mol/mol was introduced. The polymerization starts at ethylene pressure 8.5 barg and 85° C. for 1 hour. The solid product was collected by filtration and dried under vacuum to obtain a free flow polymer.

Comparative Example 33

The polymerization was conducted by the same procedure as Example 11 using Catalyst A. The result was shown in Table 9.

TABLE 8

| Example | Catalyst Name | $M_8:Al_{(MAO)}$ (mol/mol) | Activity (KgPE/molZr · h) | Viscosity at 140° C. (cP) | Density (g/mL) | Mw (g/mol) | Mn (g/mol) | Mw/Mn |
|---|---|---|---|---|---|---|---|---|
| Comparative Example 1 | Catalyst A | 0 | 3.969 | 25.3 | 0.9624 | 1,670 | 808 | 2.07 |
| Comparative Example 32 | Catalyst H-1 | 0.12 | 7.049 | 115 | 0.9723 | 3,214 | 1,251 | 2.50 |

$M_8$: Mixture of 2,3,4,5,6-pentafluorophenol and 2,6-bis(tert-butyl)-4-methylphenol The polymerization results according to Comparative Example 32 show the effect of the molar ratio of activating compound mixture to aluminum comprised in the alkylaluminoxane compared with Comparative Example 1 showing the absence of activating compound.

Comparative Example 34

The polymerization was conducted by the same procedure as Example 11 using Catalyst B-3. The result was shown in Table 9.

TABLE 9

| Example | Catalyst Name | $M_1:Al_{MAO}$ (mol/mol) | Activity (KgPE/molZr · h) | Viscosity at 140° C. (cP) | Density (g/mL) | Mw (g/mol) | Mn (g/mol) | Mw/Mn | 1-butene content (% wt) |
|---|---|---|---|---|---|---|---|---|---|
| Comparative Example 33 | Catalyst A | 0 | 2.351 | 32.5 | 0.9552 | 1,780 | 898 | 1.98 | 1.27 |
| Comparative Example 34 | Catalyst B-3 | 0.09 | 6.669 | 32.1 | 0.9530 | 1,641 | 778 | 2.11 | 1.71 |

$M_1$: 2,3,4,5,6-pentafluorophenol

The polymerization results according to Comparative Example 34 show the effect of the molar ratio of activating compound to aluminum comprised in the alkylaluminoxane compared with Comparative Example 33 showing the absence of activating compound under the condition of ethylene/1-butene copolymerization.

In an embodiment, Comparative Example 34 having the molar ratio of 2,3,4,5,6-pentafluorophenol to aluminum comprised in the alkylaluminoxane is 0.09 resulting in a higher performance of polymerization activity than Comparative Example 33 when the mixture of hydrogen and ethylene gases was introduced with the molar ratio of 0.05.

Comparative Example 35: Preparation of Heterogeneous Catalyst 8.6 mmol of solid methylaluminoxane (solidMAO, purchased from Tosoh Finechem Corporation; Al 39% wt) was diluted with 4 mL of dried toluene. 0.072 mmol of Bis(butylcyclopentadienyl)zirconium(IV)Cl$_2$ (purchased from Strem Chemicals Inc.) was dissolved with 2 mL of dried toluene. It was added dropwise into solid methylaluminoxane/toluene suspension flask. The mixture was swirled for 2 h. The heterogeneous catalyst was dried to obtain free flow solid catalyst.

TABLE 10

| Example | Catalyst Name | $M_1:Al_{MAO}$ (mol/mol) | Activity (KgPE/molZr · h) | Viscosity at 140° C. (cP) | Density (g/mL) | Mw (g/mol) | Mn (g/mol) | Mw/Mn |
|---|---|---|---|---|---|---|---|---|
| Heterogeneous catalyst | Cat Z | 0 | 1.39 | 104.6 | 0.9601 | 3334 | 937 | 3.56 |
| Comparative Example 5 | Catalyst B-4 | 0.12 | 8.488 | 23.0 | 0.9614 | 1.672 | 732 | 2.28 |

Figure 2:
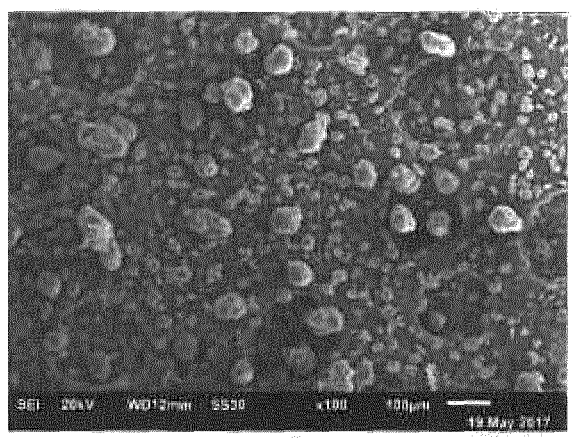

The polymer obtained from this invention (solution catalyst system, for example comparative example 5) perform good morphology without engineering operation problem (no fouling in reactor, typically polymerized ethylene using solution catalyst system usually show fouling problem). It has a morphology competitive with that from heterogeneous catalyst (as it can be taken from FIG. 1 showing an SEM image of the heterogeneous catalyst Cat Z, according to Comparative Example 35; and FIG. 2 showing an SEM image of catalyst B-4 according to comparative example 5). In other words, solution catalyst system of comparative example 5 shows good morphology and better activity than heterogeneous catalyst system.

The features disclosed in the foregoing description and in the claims may, both separately and in any combination, be material for realizing the invention in diverse forms thereof.

The invention claimed is:

1. A process for the preparation of a polyethylene wax, the process comprising the steps:
    (i) providing a catalyst solution,
        wherein the catalyst solution comprises at least one activating compound, an alkylaluminoxane and a metallocene complex, wherein a molar ratio of the activating compound to aluminum in the alkylaluminoxane is from 0.002 to 0.12; and
    (ii) polymerizing ethylene, by contacting the ethylene and the catalyst solution,
    wherein the activating compound is selected from the group consisting of phenol, 2,6-bis(tert-butyl)-4-methylphenol, 2,3,4,5,6-pentafluorophenol, 2,3,5,6-tetrafluorophenol, 2,4,6-trifluorophenol, 2,5-difluorophenol, 3,5-difluorophenol, 4-fluorophenol, 3,5 bis(trifluoromethyl)phenol, trifluoromethanol, 1,1,2,2,2-pentafluoroethanol, 2,2,2-trifluoroethanol, 1,1,1,3,3,3-hexafluoro-2-(trifluoromethyl)propan-2-ol, 1,1,1,3,3,3-hexafluoropropan-2-ol, 1,1,1-trifluoropropan-2-ol, 2,2,3,3-tetrafluoropropan-1-ol, 2,2,3,3,3-pentafluoropropan-1-ol, 1,3-difluoropropan-2-ol, methanesulfonic acid, 4-methylbenzenesulfonamide, 4-methylbenzenesulfonic acid, trifluoromethanesulfonic acid, 4-fluorophenylboronic acid, phenylboronic acid, pyridine, 1H-indole and mixtures thereof.

2. The process according to claim 1, wherein the alkylaluminoxane is selected from methylaluminoxane, i-butyl methylaluminoxane, n-butyl methylaluminoxane and n-hexyl methylaluminoxane.

3. The process according to claim 1, wherein the metallocene complex contains at least one cyclopentadienyl ligand bonded to a transition metal selected from zirconium, titanium and hafnium.

4. The process according to claim 1, wherein the metallocene complex is selected from Bis(n-butylcyclopentadienyl)zirconium(IV)dichloride and (dimethylsilylene)bis(2-methyl-4,5-benzoindenyl)zirconium(IV)dichloride.

5. The process according to claim 1, wherein the catalyst solution further comprises an aliphatic hydrocarbon solvent or an aromatic hydrocarbon solvent or mixture thereof.

6. The process according to claim 1, wherein a molar ratio of the aluminum in the alkylaluminoxane to a metal in the metallocene complex is from 25 to 200.

7. The process of claim 6, wherein the molar ratio of the aluminum in the alkylaluminoxane to the metal in the metallocene complex is from 50 to 200.

8. The process of claim 7, wherein the molar ratio of the aluminum in the alkylaluminoxane to the metal in the metallocene complex is from 50 to 100.

9. The process according to claim 1, wherein the polymerizing is slurry polymerization.

10. The process according to claim 1, wherein the polymerizing comprises contacting the catalyst solution contacting with ethylene, hydrogen and at least one comonomer having 3 to 10 carbon atoms at a temperature from 40 to 110° C. and a pressure from 1 to 12 bar in a hydrocarbon solvent.

11. The process according to claim 10, wherein a molar ratio of hydrogen to ethylene is from 0.005 to 0.05.

12. The process according to claim 1, wherein the polyethylene wax has a molecular weight from 500 to 20,000 g/mol, a molecular weight distribution from 2 to 4, a density from 0.91 to 0.98 g/mL and a viscosity from 10 to 25,000 cP.

13. The process of claim 1, wherein the molar ratio of the activating compound to the aluminum in the alkylaluminoxane is from 0.09 to 0.12.

14. The process of claim 1, wherein the molar ratio of the activating compound to the aluminum in the alkylaluminoxane is from 0.002 to 0.098.

15. The process of claim 1, wherein the molar ratio of the activating compound to the aluminum in the alkylaluminoxane is from 0.002 to 0.09.

16. The process according to claim 1, wherein the polyethylene wax has a molecular weight from 1,000 to 10,000 g/mol, a molecular weight distribution from 2 to 4, a density from 0.93 to 0.98 g/mL and a viscosity from 10 to 1,200 cP.

17. The process according to claim 14, wherein the polyethylene wax has a molecular weight from 500 to 20,000 g/mol, a molecular weight distribution from 2 to 4, a density from 0.91 to 0.98 g/mL and a viscosity from 10 to 25,000 cP.

18. The process according to claim 15, wherein the polyethylene wax has a molecular weight from 500 to 20,000 g/mol, a molecular weight distribution from 2 to 4, a density from 0.91 to 0.98 g/mL and a viscosity from 10 to 25,000 cP.

19. The process according to claim 14, wherein the polyethylene wax has a molecular weight from 1,000 to 10,000 g/mol, a molecular weight distribution from 2 to 4, a density from 0.93 to 0.98 g/mL and a viscosity from 10 to 1,200 cP.

20. The process according to claim 15, wherein the polyethylene wax has a molecular weight from 1,000 to 10,000 g/mol, a molecular weight distribution from 2 to 4, a density from 0.93 to 0.98 g/mL and a viscosity from 10 to 1,200 cP.

\* \* \* \* \*